United States Patent
Gossen et al.

(10) Patent No.: US 7,501,273 B2
(45) Date of Patent: Mar. 10, 2009

(54) PEPTIDYLARGININE DEIMINASE 6

(75) Inventors: Jan Albert Gossen, BH Oss (NL); Paul Van den Boogaart, BH Oss (NL)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 10/476,899

(22) PCT Filed: Apr. 25, 2003

(86) PCT No.: PCT/EP02/04552

§ 371 (c)(1),
(2), (4) Date: Nov. 3, 2003

(87) PCT Pub. No.: WO02/090531

PCT Pub. Date: Nov. 14, 2002

(65) Prior Publication Data
US 2004/0137598 A1 Jul. 15, 2004

(30) Foreign Application Priority Data
May 3, 2001 (EP) ................................ 01201601

(51) Int. Cl.
C12N 15/00 (2006.01)
C12N 1/21 (2006.01)
C12N 5/10 (2006.01)
C12P 21/00 (2006.01)
C07H 21/00 (2006.01)
C12Q 1/34 (2006.01)
C07K 14/00 (2006.01)
C12N 9/78 (2006.01)

(52) U.S. Cl. ................. 435/227; 435/320.1; 435/252.3; 435/325; 435/69.1; 435/18; 530/350; 536/23.2; 536/23.5

(58) Field of Classification Search ................. 435/227, 435/320.1, 252.3, 325, 69.1, 18; 536/23.1, 536/23.2, 23.5; 530/350
See application file for complete search history.

(56) References Cited

FOREIGN PATENT DOCUMENTS

| WO | 01 53339 | 7/2001 |
|---|---|---|
| WO | WO 03/010327 A2 | 2/2003 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Ausubel et al., Current Protocols in Molecular Biology, Hybridization Analysis of DNA Blots, pp. 2.10.8-2.10.11, 1993.*
Guo et al., PNAS 101(25):9205-9210, 2004.*
Kappel et al., Current Opinion in Biotechnology 3:548-553, 1992.*
Mullins et al., Hypertension 22(4):630-633, 1993.*
Mullins et al., J. Clin. Invest. 97(7):1557-1560, 1996.*
Wigley et al., Reprod. Fert. Dev. 6:585-588, 1994.*
Cameron, E., Molecular Biotechnology 7:253-265, 1997.*
Phillips A., J. Pharm. Pharmacology 53:1169-1174, 2001.*
Gardilk et al., Med. Sci. Monit. 11(4):RA110-121, 2005.*
Chavanas et al., Gene 330:19-27, 2004.*
Lewin, B., Genes IV, Oxford University Press, p. 60, 1990.*
Katsuhiko et al: "Molecular characterization of peptidylarginine deiminase in HL-60 cells induced by retinoic acid and 1alpha, 25-dihydroxyvitamin D3." Journal of Biological Chemistry, vol. 274 No. 39, pp. 37786-27792.
Rus'd Ahmed Abu et al: "Molecular cloning of cDNAs of mouse peptidylarginine deiminase type I, type III and type IV, and the expression pattern of type I in mouse." European Journal of Biochemistry, vol. 259, No. 3, Feb. 1999, pp. 660-669.
Ishigami A et al: "Molecular cloning of two novel types of peptidylarginine deiminase cDNAs from retinoic acid-treated culture of a newborn rat karatinocyte cell line", FEBS Letters 433:113-118, 1998.
Yamakoshi et al: "Cloning of cDNA encoding a novel isoform (type IV) of peptidylarginine deiminase from rat epidermis"; Biochimica et Biophysica Acta. Protein Structure and Molecular Enzymology, Elsevier, Amsterdam,, NL, vol. 1386, No. 1, Jul. 28, 1998, pp. 227-232.
Takahara et al: "Expression of Peptidylarginine deiminase in the uterine epithelial cells of mouse is dependent on estrogen"; Journal of Biological Chemistry, vol. 267, No. 1, 1992, pp. 520-525.
Database Swall Online!: Ishigami et al: Protein-Arginine Decaminase Type IV, 2000.
Database Genbank Online!: Rus'D AA et al: Mus musculus peptidyl arginine deiminase, type IV, 2000, accession #NM-011061.
Database EMBL Online!: Nakashima et al: Homo sapiens mRNA for Peptidylarginine deiminase type V, complete cds, 1999, accession #AB017919.
Database EMBL Online!: Kargul GJ et al: H3075A04-3 NIA Mouse 15k cDNA Clone Set Mus musculus cDNA clone H3075A04 3', mRNA sequence 2001, accession No. BG069310.
Altschul et al., "Gapped BLAST and PSI-BLAST: a new generation of protein database search programs," Nucleic Acids Research, vol. 25, No. 17, pp. 3389-3402 (1997).
Cooney et al., "Site-Specific Oligonucleotide Binding Represses Transcription of the Human c-myc Gene in vitro," Science, New Series, vol. 241, No. 4864, pp. 456-459 (Jul. 22, 1988).
Girbal-Neuhauser et al., "The Epitopes Targeted by the Rheumatoid Arthritis-Associated Antifilaggrin Autoantibodies are Post-translationally Generated on Various Sites of (Pro) Filaggrin by Deimination of Arginine Residues[1,2]," The Journal of Immunologists, vol. 162, pp. 585-594 (1994).
Lamensa et al., "Deimination of Human Myelin Basic Protein by a Peptidylarginine Deiminase from Bovine Brain," Journal of Neurochemisty, vol. 61, pp. 987-996 (1993).

(Continued)

*Primary Examiner*—Delia M. Ramirez

(57) ABSTRACT

A nucleotide acid sequence is provided encoding a peptidylargine deiminase 6. The gene is found to be expressed in gonads only and may be used as target for male and female contraception. Its encoded protein can be used to screen for small molecular weight modulators of the enzyme activity.

13 Claims, 5 Drawing Sheets

OTHER PUBLICATIONS

Lipman et al., "Rapid and Sensitive Protein Similarity Searches," Science, vol. 227, No. 4693, pp. 1435-1441 (Mar. 22, 1985).

Mastronardi et al., "Modifications of Myelin Basic Protein in DM20 Transgenic Mice Are Similar to those in Myelin Basic Protein from Multiple Sclerosis," J. Clin. Invest., vol. 97 No. 2, pp. 349-358 (Jan. 1996).

Nakashima et al., "Molecular Characterization of Peptidylarginine Deiminase in HL-60 Cells Induced by Retinoic Acid and 1a,25-Dihydroxyvitamin $D_3$," the Journal of Biological Chemistry, vol. 274, No. 39, pp. 27786-27792 (Sep. 24, 1999).

Pawlak et al., "Characterization of a Large Population of mRNAs from Human Testis," Genomics, vol. 26, pp. 151-158 (1995).

Rogers et al. "Peptidylarginine Deiminase of the Hair Follicle: Characterization, Localization, and Function in Keratinizing Tissues," The Journal of Investigative Dermatology, vol. 108, No. 5, pp. 700-707 (May 1997).

Senshu et al., "Preferential Deimination of Keratin K1 and Filaggrin during the Terminal Differentiation of Human Epidermis," Biochemical and Biophysical Research Communications, vol. 225, pp. 712-719 (1996).

Takahara et al., "Specific Modification of Functional Arginine Residue in Soybean Trypsin Inhibitor (Kunitz) by Peptidylarginine Deiminase," The Journal of Biological Chemistry, Col. 260, No. 14, pp. 8377-8383 (1985).

Takahara et al., "Peptidylarginine Deiminase of the Mouse," Journal of Biological Chemistry, vol. 264, No. 22, pp. 13361-13368 (1989).

Wolgemuth et al., "List of cloned mouse genes with unique expression patterns during spermatogenesis," Mammalian Genome, vol. 1. pp. 283-288 (1991).

Terakawa et al., "Three Types of Mouse Peptidylarginine Deiminase: Characterization and Tissue Distribution," J. Biochem, vol. 110, No. 4, pp. 661-666 (1991).

Nantel et al., "Spermiogenesis deficiency and germ-cell apoptosis in CREM-mutant mice," Nature, vol. 380, pp. 159-162 (Mar. 14, 1996).

Remington's Pharmaceutical Sciences, 16th Edition, Chapter 84, Avis "Parenteral Preparations," & Chapter 85, Turco et al., "Intravenous Admixtures", pp. 1463-1497 (1980).

Dong et al., "Growth differentiation factor-9 is required during early ovarian folliculogenesis," Letters To Nature, vol. 383, pp. 531-535 (Oct. 10, 1996).

* cited by examiner

Adult: 1B11-antisense

7 d old: 1B11-antisense

Adult: 1B11-sense

7 d old: 1B11-sense

SEQUENCE LISTING

<160> NUMBER OF SEQ ID NOS: 15

<210> SEQ ID NO 1
<211> LENGTH: 682
<212> TYPE: PRT
<213> ORGANISM: Mus musculus

<400> SEQUENCE: 1

```
Met Ser Phe Gln Asn Ser Leu Ser Leu Ser Leu Val Asn Pro Thr His
  1               5                  10                  15
Ala Leu Cys Met Val Gly Met Glu Ile Thr Leu Asp Ile Ser Lys Cys
             20                  25                  30
Ala Pro Asp Lys Cys Lys Ser Phe Thr Ile Arg Gly Ser Pro Arg Ile
             35                  40                  45
Leu Ile His Ile Ser Ser Val Ile Ala Gly Lys Glu Asp Thr Val
         50                  55                  60
Val Trp Arg Ser Met Asn His Pro Thr Val Ala Leu Val Arg Met Val
 65                  70                  75                  80
Ala Pro Ser Pro Thr Val Asp Glu Asp Lys Val Leu Val Ser Tyr Phe
                 85                  90                  95
Cys Pro Asp Gln Glu Val Pro Thr Ala Thr Val Leu Phe Leu Thr
                100                 105                 110
Gly Ile Glu Ile Ser Leu Glu Ala Asp Ile Tyr Arg Asp Gly Gln Leu
            115                 120                 125
Asp Met Pro Ser Asp Lys Gln Ala Lys Lys Trp Met Trp Gly Met
        130                 135                 140
Asn Gly Trp Gly Ala Ile Leu Leu Val Asn Cys Ser Pro Asn Ala Val
145                 150                 155                 160
Gly Gln Pro Asp Glu Gln Ser Phe Gln Glu Gly Pro Arg Glu Ile Gln
                165                 170                 175
Asn Leu Ser Gln Met Asn Val Thr Val Glu Gly Pro Thr Ser Ile Leu
                180                 185                 190
Gln Asn Tyr Gln Leu Ile Leu His Thr Ser Glu Glu Ala Lys Lys
            195                 200                 205
Thr Arg Val Tyr Trp Ser Gln Arg Gly Ser Ser Ala Tyr Glu Leu Val
    210                 215                 220
Val Gly Pro Asn Lys Pro Val Tyr Leu Leu Pro Thr Phe Glu Asn Arg
225                 230                 235                 240
Arg Lys Glu Ala Phe Tyr Val Glu Ala Thr Glu Phe Pro Ser Pro Ser
                245                 250                 255
Phe Ser Gly Leu Ile Ser Leu Ser Leu Ser Leu Val Glu Lys Ala His
                260                 265                 270
Asp Glu Cys Ile Pro Glu Ile Pro Leu Tyr Lys Asp Thr Val Met Phe
            275                 280                 285
Arg Val Ala Pro Tyr Ile Phe Met Pro Ser Thr Gln Met Pro Leu Glu
        290                 295                 300
Val Tyr Leu Cys Arg Glu Leu Gln Leu Gln Gly Phe Val Asp Ser Val
305                 310                 315                 320
Thr Lys Leu Ser Glu Lys Ser Lys Val Gln Val Lys Val Tyr Glu
                325                 330                 335
Asp Pro Asn Arg Gln Ser Lys Trp Leu Gln Asp Glu Met Ala Phe Cys
            340                 345                 350
Tyr Thr Gln Ala Pro His Lys Thr Val Ser Leu Ile Leu Asp Thr Pro
        355                 360                 365
Arg Val Ser Lys Leu Glu Asp Phe Pro Met Lys Tyr Thr Leu Thr Pro
    370                 375                 380
Gly Ser Gly Tyr Leu Ile Arg Gln Thr Glu Asp His Arg Val Ala Ser
385                 390                 395                 400
Leu Asp Ser Ile Gly Asn Leu Met Val Ser Pro Pro Val Lys Ala Gln
```

-continued

```
                    405                 410                 415
Gly Lys Asp Tyr Pro Leu Gly Arg Val Leu Ile Gly Gly Ser Phe Tyr
                420                 425                 430

Pro Ser Ser Glu Gly Arg Asp Met Asn Lys Gly Leu Arg Glu Phe Val
            435                 440                 445

Tyr Ala Gln Gln Val Gln Ala Pro Val Glu Leu Phe Ser Asp Trp Leu
        450                 455                 460

Met Thr Gly His Met Asp Gln Phe Met Cys Phe Val Pro Thr Asn Asp
465                 470                 475                 480

Lys Asn Asn Asp Gln Lys Asp Phe Arg Leu Leu Leu Ala Ser Pro Ser
                485                 490                 495

Ala Cys Phe Glu Leu Phe Glu Gln Lys Gln Lys Glu Gly Tyr Gly Asn
            500                 505                 510

Val Thr Leu Phe Glu Asp Ile Gly Ala Glu Gln Leu Leu Ser Asn Gly
        515                 520                 525

Arg Glu Ser Lys Thr Ile Ser Gln Ile Leu Ala Asp Lys Ser Phe Arg
    530                 535                 540

Glu Gln Asn Thr Tyr Val Glu Lys Cys Ile Ser Leu Asn Arg Thr Leu
545                 550                 555                 560

Leu Lys Thr Glu Leu Gly Leu Glu Asp Lys Asp Ile Ile Leu Ile Pro
                565                 570                 575

Gln Leu Phe Cys Leu Glu Gln Leu Thr Asn Val Pro Ser Asn Gln Gln
            580                 585                 590

Ser Thr Lys Leu Phe Ala Arg Pro Tyr Phe Pro Asp Met Leu Gln Ile
        595                 600                 605

Ile Val Leu Gly Lys Asn Leu Gly Ile Pro Lys Pro Phe Gly Pro Lys
    610                 615                 620

Ile Asn Gly Thr Cys Cys Leu Glu Glu Lys Val Cys Gly Leu Leu Glu
625                 630                 635                 640

Pro Leu Gly Leu Lys Cys Thr Phe Ile Asp Asp Phe Asp Cys Tyr Leu
                645                 650                 655

Ala Asn Ile Gly Asp Val Cys Ala Ser Ala Ile Ile Asn Arg Val Pro
            660                 665                 670

Phe Ala Phe Lys Trp Trp Lys Met Thr Pro
        675                 680

<210> SEQ ID NO 2
<211> LENGTH: 2055
<212> TYPE: DNA
<213> ORGANISM: Mus musculus

<400> SEQUENCE: 2
cagccatgtc ttttcagaac tcactcagcc tgtctctggt caatcccacc catgccctct      60
gcatggtagg catggaaatc accttggaca tcagcaagtg tgcaccagac aagtgcaagt     120
ctttcaccat ccgtggttcc cccaggatct tgatccacat ctctagctcc gtcatcgctg     180
gcaaagagga cactgtggtc tggaggtcaa tgaaccatcc acagtggca ttggtgagga     240 tggtggcgcc cagccccact gtggatgaag acaaggtgct ggtctcctac ttctgtcctg     300
accaagaagt ccccacggcc acagctgtgc tgtttctcac cggcatcgag atctccctgg     360
aggcagacat ctatcgagat ggacaactgg acatgccaag tgataagcaa gctaagaaaa     420
aatggatgtg gggtatgaac ggctggggag ccatcctgct tgtgaattgt agccctaatg     480
ctgtgggcca gcctgatgaa cagtcctttc aggagggccc cagagaaata cagaacctgt     540
```

-continued

```
ctcagatgaa tgtaactgtg gagggcccca ccagcatcct acagaattac cagttgatcc      600
tacatacctc cgaagaagag gcgaagaaga caagagtcta ctggtctcag agaggctcct      660
ctgcgtatga actggtggtg ggacccaaca agcctgtcta tctcctgcct acctttgaga      720
accgtaggaa agaggctttc tacgtagaag ccacggaatt cccatctccc agcttctcgg      780
gcctgatctc cttgtcactc tccctagtag aaaaggctca cgacgagtgc atcccagaga      840
ttccgctcta taaggataca gtgatgttcc gggtggcacc ttatatcttc atgcccagca      900
cccagatgcc tctagaggtt tacctgtgca gggagctaca gctgcaaggc tttgtggact      960
cagtgaccaa gctgagcgag aagagcaaag tgcaggtggt aaaggtctat gaggaccccca     1020
accgccagag caagtggctc caggacgaga tggctttctg ctatactcag gctcctcaca     1080
agacggtgtc attgatcctt gacaccccaa gggtttccaa gctggaagac ttccccatga     1140
aatacacact gaccctggc tctggctacc tgatccgaca aactgaggac accgggtgg       1200
ctagcctgga ttcatcggg aacctgatgg tatctccgcc tgtcaaggct cagggcaaag     1260
actaccctct agggagggtc ctcattggtg gcagcttta ccccagctct gagggccggg      1320
acatgaacaa gggcctgcga gaattcgtgt atgcccagca ggtgcaggcc cctgtggaac     1380
tcttctcgga ctggctgatg accggtcaca tggatcaatt catgtgcttt gtccctacca     1440
atgataaaaa caacgaccag aaggacttcc gcctgctgct ggccagcccc agtgcctgct     1500
ttgagctgtt cgaacagaag cagaaggaag gctatgggaa cgtgaccctg tttgaagaca     1560
ttggagcaga acagctcctt tctaatggga gggagagcaa aactatttcc caaatcctgg     1620
ctgacaagag ttttcgagag cagaacacct atgttgagaa gtgtatcagc ctgaaccgca     1680
ccctcctgaa gacagaactg ggattggagg acaaggacat catcctgatc ccgcagctct     1740
tctgcctgga gcagctgacg aatgtcccct ccaaccagca gagcaccaaa ctcttcgcga     1800
ggccgtactt ccccgacatg ctgcagataa tcgtgttggg caagaacctt ggaatcccca     1860
agcccctttgg gcccaaaatc aatggcacct gctgcctaga agagaaagtg tgtggattac     1920
tggagcccct gggtctcaag tgcaccttca ttgatgattt tgactgctac ctggccaaca     1980
taggggacgt ctgtgccagt gccatcataa acagggtgcc atttgcattc aagtggtgga     2040
agatgacccc ataaa                                                       2055
```

<210> SEQ ID NO 3
<211> LENGTH: 686
<212> TYPE: PRT
<213> ORGANISM: Homo sapiens

<400> SEQUENCE: 3

```
Met Ser Phe Gln Ser Ile Ile His Leu Ser Leu Asp Ser Pro Val His
  1               5                  10                  15

Ala Val Cys Val Leu Gly Thr Glu Ile Cys Leu Asp Leu Ser Gly Cys
                 20                  25                  30

Ala Pro Gln Lys Cys Gln Cys Phe Thr Ile His Gly Ser Gly Arg Val
             35                  40                  45

Leu Ile Asp Val Ala Asn Thr Val Ile Ser Glu Lys Glu Asp Ala Thr
         50                  55                  60

Ile Trp Trp Pro Leu Ser Asp Pro Thr Tyr Ala Thr Val Lys Met Thr
 65                  70                  75                  80

Ser Pro Ser Pro Ser Val Asp Ala Asp Lys Val Ser Val Thr Tyr Tyr
                 85                  90                  95

Gly Pro Asn Glu Asp Ala Pro Val Gly Thr Ala Val Leu Tyr Leu Thr
```

-continued

```
            100                 105                 110
Gly Ile Glu Val Ser Leu Glu Val Asp Ile Tyr Arg Asn Gly Gln Val
            115                 120                 125
Glu Met Ser Ser Asp Lys Gln Ala Lys Lys Trp Ile Trp Gly Pro
130                 135                 140
Ser Gly Trp Gly Ala Ile Leu Leu Val Asn Cys Asn Pro Ala Asp Val
145                 150                 155                 160
Gly Gln Gln Leu Glu Asp Lys Lys Thr Lys Val Ile Phe Ser Glu
            165                 170                 175
Glu Ile Thr Asn Leu Ser Gln Met Thr Leu Asn Val Gln Gly Pro Ser
            180                 185                 190
Cys Ile Leu Lys Lys Tyr Arg Leu Val Leu His Thr Ser Lys Glu Glu
            195                 200                 205
Ser Lys Lys Ala Arg Val Tyr Trp Pro Gln Lys Asp Asn Ser Ser Thr
210                 215                 220
Phe Glu Leu Val Leu Gly Pro Asp Gln His Ala Tyr Thr Leu Ala Leu
225                 230                 235                 240
Leu Gly Asn His Leu Lys Glu Thr Phe Tyr Val Glu Ala Ile Ala Phe
            245                 250                 255
Pro Ser Ala Glu Phe Ser Gly Leu Ile Ser Tyr Ser Val Ser Leu Val
            260                 265                 270
Glu Glu Ser Gln Asp Pro Ser Ile Pro Glu Thr Val Leu Tyr Lys Asp
            275                 280                 285
Thr Val Val Phe Arg Val Ala Pro Cys Val Phe Ile Pro Cys Thr Gln
            290                 295                 300
Val Pro Leu Glu Val Tyr Leu Cys Arg Glu Leu Gln Leu Gln Gly Phe
305                 310                 315                 320
Val Asp Thr Val Thr Lys Leu Ser Glu Lys Ser Asn Ser Gln Val Ala
            325                 330                 335
Ser Val Tyr Glu Asp Pro Asn Arg Leu Gly Arg Trp Leu Gln Asp Glu
            340                 345                 350
Met Ala Phe Cys Tyr Thr Gln Ala Pro His Lys Thr Thr Ser Leu Ile
            355                 360                 365
Leu Asp Thr Pro Gln Ala Ala Asp Leu Asp Glu Phe Pro Met Lys Tyr
            370                 375                 380
Ser Leu Ser Pro Gly Ile Gly Tyr Met Ile Gln Asp Thr Glu Asp His
385                 390                 395                 400
Lys Val Ala Ser Met Asp Ser Ile Gly Asn Leu Met Val Ser Pro Pro
            405                 410                 415
Val Lys Val Gln Gly Lys Glu Tyr Pro Leu Gly Arg Val Leu Ile Gly
            420                 425                 430
Ser Ser Phe Tyr Pro Ser Ala Glu Gly Arg Ala Met Ser Lys Thr Leu
            435                 440                 445
Arg Asp Phe Leu Tyr Ala Gln Gln Val Gln Ala Pro Val Glu Leu Tyr
            450                 455                 460
Ser Asp Trp Leu Met Thr Gly His Val Asp Glu Phe Met Cys Phe Ile
465                 470                 475                 480
Pro Thr Asp Asp Lys Asn Glu Gly Lys Lys Gly Phe Leu Leu Leu Leu
            485                 490                 495
Ala Ser Pro Ser Ala Cys Tyr Lys Leu Phe Arg Glu Lys Gln Lys Glu
            500                 505                 510
Gly Tyr Gly Asp Ala Leu Leu Phe Asp Glu Leu Arg Ala Asp Gln Leu
            515                 520                 525
```

```
Leu Ser Asn Gly Arg Glu Ala Lys Thr Ile Asp Gln Leu Leu Ala Asp
    530                 535                 540

Glu Ser Leu Lys Lys Gln Asn Glu Tyr Val Glu Lys Cys Ile His Leu
545                 550                 555                 560

Asn Arg Asp Ile Leu Lys Thr Glu Leu Gly Leu Val Glu Gln Asp Ile
                565                 570                 575

Ile Glu Ile Pro Gln Leu Phe Cys Leu Glu Lys Leu Thr Asn Ile Pro
            580                 585                 590

Ser Asp Gln Gln Pro Lys Arg Ser Phe Ala Arg Pro Tyr Phe Pro Asp
        595                 600                 605

Leu Leu Arg Met Ile Val Met Gly Lys Asn Leu Gly Ile Pro Lys Pro
    610                 615                 620

Phe Gly Pro Gln Ile Lys Gly Thr Cys Cys Leu Glu Glu Lys Ile Cys
625                 630                 635                 640

Cys Leu Leu Glu Pro Leu Gly Phe Lys Cys Thr Phe Ile Asn Asp Phe
                645                 650                 655

Asp Cys Tyr Leu Thr Glu Val Gly Asp Ile Cys Ala Cys Ala Asn Ile
            660                 665                 670

Arg Arg Val Pro Phe Ala Phe Lys Trp Trp Lys Met Val Pro
        675                 680                 685

<210> SEQ ID NO 4
<211> LENGTH: 2092
<212> TYPE: DNA
<213> ORGANISM: Homo sapiens

<400> SEQUENCE: 4
tagcgtggag ggccgagcca tgtccttcca gagtatcatc cacctgtccc tggacagccc    60
tgtccatgcc gtttgtgtgt tgggcacaga atctgcttg  atctcagcg ggtgtgcccc   120 ccagaagtgc cagtgcttca ccatccatgg ctctgggagg tcttgatcg  atgtggccaa   180 cacggtgatt tctgagaagg aggacgccac catctggtgg ccctgtctg  atcccacgta   240 cgccacagtg aagatgacat cgcccagccc ttccgtggat gcggataagg tctcggtcac   300
atactatggg cccaacgagg atgccccgt  gggcacagct gtgctgtacc tcactggcat   360
tgaggtctct ctagaggtag acatctaccg caatgggcaa gttgagatgt caagtgacaa   420
acaggctaag aaaaaatgga tctggggtcc cagcggttgg ggtgccatcc tgcttgtgaa   480
ttgcaaccct gctgatgtgg gccagcaact tgaggacaag aaaaccaaga aagtgatctt   540
ttcagaggaa ataacgaatc tgtcccagat gactctgaat gtccaaggcc ccagctgtat   600
cttaaagaaa tatcggctag tcctccatac ctccaaggaa gagtcgaaga aggcgagagt   660
ctactggccc caaaaagaca actccagtac ctttgagttg gtgctggggc ccgaccagca   720
cgcctatacc ttggccctcc tcgggaacca cttgaaggag actttctacg ttgaagctat   780
agcattccca tctgccgaat ctcaggcct  catctcctac tctgtgtccc tggtggagga   840
gtctcaagac ccgtcaattc cagagactgt gctgtacaaa gacacggtgg tgttccgggt   900
ggctccctgt gtcttcattc cctgtaccca ggtgcctctg gaggtttacc tgtgcaggga   960
gctgcagctg cagggttttg tggacacagt gacgaagctg agtgagaaga gcaacagcca  1020
ggtggcatct gtctatgagg accccaaccg cctgggcagg tggctccagg atgagatggc  1080
cttctgctac acccaggctc cccacaagac aacgtccttg atcctcgaca cacctcaggc  1140
cgccgatctc gatgagttcc ccatgaagta ctcactgagc cctggtattg gctacatgat  1200
```

-continued

```
ccaggacact gaggaccata aagtggccag catgggattcc attgggaacc tgatggtgtc    1260
cccacctgtc aaggtccaag ggaaagagta cccgctgggc agagtcctca ttggcagcag    1320
cttttacccc agcgcagagg gccgggccat gagtaagacc ctccgagact tcctctatgc    1380
ccagcaggtc caagcgccgg tggagctcta ctcagattgg ctaatgactg ccacgtggga    1440
tgagttcatg tgcttcatcc ccacagatga caagaatgag ggcaaaaagg cttcctgct     1500 gctcctggcc agccccagtg cctgctataa actgttccga gagaaacaga aggaaggcta    1560
tggcgacgct cttctgtttg atgagcttag agcagatcag ctcctgtcta atggaaggga    1620
agccaaaacc atcgaccaac ttctggctga tgaaagcctg aagaagcaga atgaatacgt    1680
ggagaagtgc attcacctga accgtgacat cctgaagacg gagctgggcc tggtggaaca    1740
ggacatcatc gagattcccc agctgttctg cttggagaag ctgactaaca tccctctga    1800 ccagcagccc aagaggtcct tgcgaggcc atacttccct gacctgttgc ggatgattgt     1860
gatgggcaag aacctgggga tccccaagcc ttttgggccc caaatcaagg ggacctgctg    1920
cctggaagaa aagatttgct gcttgctgga gcccctgggc ttcaagtgca ccttcatcaa    1980
tgactttgac tgttacctga cagaggtcgg agacatctgt gcctgtgcca acatccgccg    2040
ggtgcccttt gccttcaaat ggtggaagat ggtaccttag acccaggccc ta             2092
```

```
<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ttgacaccag accaactggt aatg                                              24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ggtggcgacg actcctggag cccg                                              24

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gttttcccag tcacgac                                                      17

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
```

Primer

<400> SEQUENCE: 8
cgtcagctgc tccagcagaa                    20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
gatttaggtg acactatag                     19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
gtgcggttca ggctgataca                    20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
agcgtggagg gccgagccat g                  21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
agggcctggg tctaaggtac catc                24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ctgatgaccg gcacatggat                    20

<210> SEQ ID NO 14

```
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ggcggttggg gtcctcatag                                                  20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
gccatcctgc ttgtgaattg                                                  20
```

PEPTIDYLARGININE DEIMINASE 6

This application is the National Stage of International Application No. PCT/EP02/04552, filed Apr. 25, 2002.

The current invention relates to polynucleotides encoding peptidylarginine deiminase 6, cells transfected with these polynucleotides, proteins produced by these cells as well as to a method to produce these proteins and its modulators.

Peptidylarginine deiminases (PADs) are a family of post-translational modification enzymes which convert peptidylarginine into citrulline in a $Ca^{2+}$-dependent manner. Enzymatic deimination in vitro changes the functional properties of various proteins and alters their secondary and tertiary structures.

Sofar, five isoforms of PAD have been identified showing a broad tissue distribution. Mouse PAD1 is detected in the epidermis and uterus (Rus'd, A. A. et al. 1990, Eur. J. Biochem. 259, 660–669); murine PAD2 is widely expressed in various tissues such as brain, pituitary, spinal cord, salivary gland, pancreas, skeletal muscle, uterus, spleen, stomach and thymus (Takahara, H. et al. 1989, J. Biol. Chem. 264, 13361–13368); murine PAD3 is expressed in epidermis and hair follicles (Terakawa, H. et al. 1991, J. Biochem. (Tokyo) 110, 661–666); PAD4 (rat) is an ubiquitous enzyme being expressed in the pancreas, spleen, ovary, liver, lung, stomach, kidney, uterus, dermis, brain, heart and epidermis (Yamakoshi, A. et al. 1998, Biochim. Biophys. Acta 1386, 227–232); human PAD5 finally has been isolated as a new family member from a myeloid leukemia cell line, but its tissue distribution has not been further determined (Nakashima, K. et al. 1999, J. Biol. Chem. 274,27786–27792).

Little is known about the physiological functions of PAD. In brain, myelin basic protein is a natural substrate and therefore, PAD plays an important part in the central nervous system. Moreover, when disregulated PAD plays a role in the aetiology of multiple sclerosis (Mastronardi, F. G. et al. 1996, Clin. Invest. 97, 349–358). PAD in the epidermis seems to be involved in the terminal processing of filaggrin, which indirectly is important for the maintenance of moisture in the upper stratum corneum (Senshu, T. et al. 1996, Biochem. Biophys. Res. Commun. 225, 712–719). Again, disregulation of this PAD may play a role in the aetiology of rheumatoid arttritis (Girbal-Neuhauser, E. et al. 1999, J. Immunol. 162, 585–594). In hair follicles finally the solubility of trichohyalin seems to be influenced by PAD; the function of this remains to be determined (Rogers, G. E. et al. 1997, J. Invest. Dermatol. 108, 700–707).

We now have found a novel PAD, which is called PAD6. The transcript has been found in mouse oocytes. Its human homologue is also described herein. The protein was found to be expressed exclusively in oocytes/ovary and testes.

Genes that are expressed specifically in male and/or female gametes may provide novel molecular targets for male and female contraception. For testis, large numbers of gene sequences expressed uniquely in germ cells have been described (Pawlak, A. et al. 1995 Genomics 26, 151–1588; Wolgemuth D. J. and Watrin F. 1991 Mamm Genome 1, 283–817). In contrast, only a few genes specifically expressed in oocytes thus far have been identified. The majority of gamete specific gene sequences identified are likely to have an essential function due to their specific expression in gametes. The latter is confirmed by studies using knockout animals indicating that gene inactivation of testis and oocyte specific genes generally results in male and/or female infertility but does not result in additional pathology in other organs and tissues (Dong, J. et al. 1996 Nature 383, 531–535; Nantel, F. et al. 1996, Nature 380, 159–162). These data provide further evidence for the specific and essential role of these genes during gametogenesis. This underlines the importance of tissue specificity as selection criteron for molecular targets for fertility regulation.

It will be clear that there is a great need for the elucidation of genes involved in fertility regulation in order to unravel the various roles these genes may play in infertility. A better knowledge of the genes involved in different stages of female and male fertility e.g. in gametogenesis and their activity and expression regulation might help to create a better insight in infertility disorders. This could eventually lead to the identification of activity modulators to be used in either inl vivo or in vitro therapeutic protocols.

The present invention provides for such a gene. More specific, the present invention provides for a polynucleotide sequence encoding peptidylarginine deiminase 6 (PAD6). Preferably the polynucleotide is of mammalian origin, preferably mouse, more preferably human. The RNA is expressed exclusively in reproductive organs.

The most preferred polynucleotide sequences are those encoding SEQ ID NO: 1 or SEQ ID NO:3.

The invention also includes the entire mouse mRNA sequence as indicated in SEQ ID NO:2 and more specifically the open reading frame corresponding to nucleotide sequence 6-2051 of SEQ ID NO:2. This sequence encodes a protein of 692 amino acids (SEQ ID NO:1). In addition the invention includes the entire human mRNA sequence as indicated in SEQ ID NO:4 and the open reading frame corresponding to nucleotide sequence 20-2077 of SEQ ID NO:4 This sequence encodes a protein of 686 amino acids (SEQ ED NO:3). To accommodate codon variability, the invention also includes polynucleotide sequences coding for the same amino acid sequences as the sequences disclosed herein. The sequence information as provided herein should not be so narrowly construed as to require exclusion of erroneously identified bases. The specific sequence disclosed herein can readily be used to isolate the complete genes of several other species or allelic variants. The sequence can e.g. be used to prepare probes or as a source to prepare synthetic oligonucleotides to be used as primers in DNA amplification reactions allowing the isolation and identification of the complete variant genes. In particular, polynucleotides hydridizing under stringent washing conditions with a probe prepared with PCR under standard conditions using SEQ ID NO:14 and SEQ ID NO:15 with cDNA from mammalian origin as a template, preferably human or mouse, are part of the invention. Such a probe (and its complementary sequence) is is identified e.g by the nucleotides 464–1052 of SEQ ID NO:4.

The complete genetic sequence can be used in the preparation of vector molecules for expression of the protein in suitable host cells.

Thus, in one aspect, the present invention provides for isolated polynucleotides encoding the novel PAD6 protein. Preferably the PAD6 is of human origin, but also orthologs form part of the invention.

The DNA according to the invention may be obtained from cDNA. The tissues preferably are from mammalian origin, more preferably from human origin. Preferably ribonucleic acids are isolated from oocytes or testes. Alternatively, the coding sequence might be genomic DNA, or prepared using DNA synthesis techniques. The polynucleotide may also be in the form of RNA. If the polynucleotide is DNA, it may be in single stranded or double stranded form. The single strand might be the coding strand or the non-coding (anti-sense) strand.

The DNA according to the invention will be very useful for in vivo or in vitro expression of the novel protein according to the invention in sufficient quantities and in substantially pure form.

The present invention further relates to polynucleotides having slight variations or having polymorphic sites. Polynucleotides having slight variations may encode variant polypeptides which retain the same biological function or activity as the natural, mature protein. Polymorphic sites are useful for diagnostic purposes.

In another aspect, the invention provides for a method to isolate a polynucleotide comprising the steps of: a) hybridizing a polynucleotide according to the present invention, or its complement, under stringent conditions against nucleic acids being (genomic) DNA RNA, or cDNA isolated preferably from tissues which highly express the polynucleotide of interest and b) isolating said nucleic acids by methods known to a skilled person in the art. The tissues preferably are from human origin. Preferably ribonucleic acids are isolated from oocytes, ovaria or testes. The hybridization conditions are preferably highly stringent.

According to the present invention the term "stringent" means washing conditions of 1×SSC, 0.1% SDS at a temperature of 65° C.; highly stringent conditions refer to a reduction in SSC towards 0.3×SSC, more preferably to 0.1×SSC. Preferably the first two washings are subsequently carried out twice each during 15–30 minutes. If there is a need to wash under highly stringent conditions an additional wash with 0.1×SSC is performed once during 15 minutes. Hybridization can be performed e.g. overnight in 0.5M phosphate buffer pH7.5/7% SDS at 65° C.

As an alternative the method to isolate the gene might comprise gene amplification methodology using primers derived from the nucleic acid according to the invention. Complete cDNAs might also be obtained by combining clones obtained by e.g. hybridization with e.g. RACE cDNA clones.

Also portions of the coding sequences coding for a functional polypeptide are part of the invention as well as allelic and species variations thereof. Sometimes, a gene is expressed in a certain tissue as a splicing variant, resulting in an altered 5' or 3' mRNA or the inclusion or exclusion of one or more exon sequences. These sequences as well as the proteins encoded by these sequences all are expected to perform the same or similar functions and form also part of the invention.

The invention also provides for peptidylarginine deiminase 6 SPAD6). Preferably the protein has a mammalian amino acid sequence, more preferably a human sequence. Most preferred are the sequences as described in SEQ ID NOs: 1 or 3. Expression can be obtained by introduction of vector molecules comprising a polynucleotide encoding PAD6 into suitable host cells. The cells can be cultured and the protein can be isolated using methods known to the person skilled in the art.

In still another aspect of the invention there are provided functional equivalents that is polypeptides encoding PAD6 activities and comprising essentially the same SEQ ID NO:1 or 3 sequence or parts thereof having variations of the sequence while still maintaining functional characteristics.

The variations that can occur in a sequence may be demonstrated by (an) amino acid difference(s) in the overall sequence or by deletions, substitutions, insertions, inversions or additions of (an) amino acid(s) in said sequence. Amino acid substitutions that are expected not to essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science, 1985 227, 1435–1441) and determining the functional similarity between homologous polypeptides. It will be clear that also polynucleotides coding for such variants are part of the invention.

Thus, in another aspect of the invention there are provided polypeptides comprising SEQ ID NO:1 or SEQ ID NO:3 or but also polypeptides with a similarity of 80%, preferably 90%, more preferably 95%.

As used herein the term similarity is as defined in NCBI-BLAST 2.0.10 [Aug-26-1999] (Altschul, Stephen F., Thomas L. Madden, Alejandro A. Schaffer, Jinghui Zhang, Zheng Zhang, Webb Miller, and David J. Lipman (1997) "Gapped BLAST and PSI-BLAST: a new generation of protein database search programs", Nucleic Acids Res. 25, 3389–3402). The program is used to search for sequence alignments using default settings. For amino acid alignments the BLOSUM62 matrix is used as a default and the similarity is indicated as the number of positives. No filtering of low compositional complexity is included.

Also portions of such polypeptides still capable of conferring biological effects are included. Especially portions which still are capable of converting arginine to citrulline form part of the invention. Such proteins or functional parts thereof may be functional per se, e.g. in solubilized form or they may be linked to other polypeptides (e.g. to direct it to specific subcellular compartments, to increase its stability or to facilitate its purification), either by known biotechnological ways or by chemical synthesis, to obtain chimeric proteins.

It will be clear that also polynucleotides encoding such variant polypeptides are included in the invention.

A wide variety of host cell and cloning vehicle combinations may be usefully employed in cloning the nucleic acid sequence coding for the polypeptide according to the invention.

Suitable expression vectors are for example bacterial or yeast plasmids, wide host range plasmids and vectors derived from combinations of plasmid and phage or virus DNA. Vectors derived from chromosomal DNA are also included. Furthermore an origin of replication and/or a dominant selection marker can be present in the vector according to the invention. The vectors according to the invention are suitable for transforming a host cell.

Vehicles for use in expression of the protein or parts thereof of the present invention will further comprise control sequences operably linked to the nucleic acid sequence coding for the protein. Such control sequences generally comprise a promoter sequence and sequences, which regulate and/or enhance expression levels. Of course control and other sequences can vary depending on the host cell selected.

Recombinant expression vectors comprising the DNA of the invention as well as cells transfected with said DNA or said expression vector, either transiently or stable, also form part of the present invention.

Suitable host cells according to the invention are bacterial host cells, yeast and other fungi, plant or animal host such as Chinese Hamster Ovary cells, monkey cells, or human cells; Thus, a host cell which comprises the DNA or expression vector according to the invention is also within the scope of the invention. The engineered host cells can be cultured in conventional nutrient media which can be modified e.g. for appropriate selection, amplification or induction of transcription. The culture conditions such as temperature, pH, nutrients etc. are well known to those ordinary skilled in the art.

The techniques for the preparation of the DNA or the vector according to the invention as well as the transformation or transfection of a host cell with said DNA or vector are standard and well known in the art, see for instance Sambrook et al., Molecular Cloning: A laboratory Manual. 2nd Ed., Cold Spring Harbor Laboratory, Cold Spring Harbor, N.Y., 1989.

The protein according to the invention can be recovered and purified from recombinant cell cultures by common biochemical purification methods (as described in Guide to Protein purification. Edited by Murray P. Deutscher. (1990) Methods in Enzymology. Vol 182. Academic Press, inc. San Diego Calif. 92101. Harcourt Brace Jovanovich, Publishers). including ammonium sulfate precipitation, extraction, chromatography such as hydrophobic interaction chromatography, cation or anion exchange chromatography or affinity chromatography and high performance liquid chromatography. If necessary, also protein refolding steps can be included. Alternatively the protein can be expressed and purified as a fusion protein containing ("tags") which can be used for affinity purification.

Regulation of the activity of the protein according to the invention is useful in vivo for the control of follicular recruitment, but also of growth and maturation of oocytes and/or follicles. Inhibition of these processes in vivo can be used to delay (premature) menopause and/or as a contraceptive. In addition, the protein can be employed for in vitro maturation and growth of follicles e.g. from frozen ovarian tissue.

PAD gene products according to the present invention can be used for the in vivo or in vitro identification of novel substrates or analogs thereof. For this purpose e.g. peptidyl arginine deiminase assay studies can be performed with cells transformed with DNA according to the invention or an expression vector comprising DNA according to the invention, said cells expressing the PAD6 gene products according to the invention. Alternatively also the PAD6 protein itself or the substrate-binding domains thereof can be used in an assay for the identification of functional substrates or analogs.

Methods to determine peptidyl arginine deiminase activity of expressed gene products in in vitro and in vivo assays to determine biological activity of gene products are well known. See e.g. Lamensa, F. E. W. and Moscarello, M. A. 1993 J. Neurochem. 61, 987–996. In this assay arginine in α-Nbenzoyl-Larginine ethyl ester (BAEE) is converted in citrulline which can easily be measured after precipitation with perchloric acid.

Another example of determining the enzymatic activity of PAD6 makes use of the inactivation of a protein e.g. Soybean Trypsin Inhibitor (STI) (Talcahara, H. et al. 1985, J. Biol. Chem. 260, 8378–8383. When an essential arginine in STI is converted into citrulline it is no longer able to inhibit the proteolytic activity of trypsin. This can be used as the basis for a two-step assay for the determination of PAD activity. The assay consists of two steps. In the first reaction PAD converts the arginine (position 63) in STI into a citrulline inactivating the STI. In the second reaction trypsin and a fluorescent substrate are added and trypsin activity is measured.

Alternatively modulation of the PAD6 activity can also be obtained by down-regulation of the expression level of the protein e.g. by using anti-sense nucleic acids through triple-helix formation (Cooney et al., 1988, Science 241, 456–459) or by binding to the mRNA, or by influencing mRNA stability or protein interactions by small molecules. This in itself could also lead to regulation of fertility i.e. contraception or treatment of infertility.

Thus, the present invention provides for a method for identifying compounds that affect the enzymatic function of the protein according to the invention. The method comprises the steps of a) contacting the PAD6 protein with an arginine containing substrate b) contacting said mixture with a test compound c) measuring the arginine to citrulline conversion and d) comparing said conversion with peptidylarginine deiminase activity in the absence of a test compound.

The arginine to citrulline conversion can easily be measured e.g. by analytical methods like HPLC, altered proteolytic sensitivity of the peptide, change in activity properties of the peptide or specific antibody recognition. As a substrate peptides or proteins comprising arginine can be used, but also synthetic compounds such as α-N-benzoyl-L-arginine ethyl ester can be used. However, the amino and carboxyl groups have to be substituted or have to be in a peptide bonded form.

Alternatively, the present invention provides for a method to identify compounds that modulate the PAD6 mRNA stability or the PAD6 expression levels.

The present invention thus provides for a quick and economic method to screen for therapeutic agents for fertility control related to the activity of PAD6. The method according to the invention furthermore provides for the selection of selective therapeutic agents discriminating between different peptidylarginine deiminases thus leading to a more effective therapeutic agent and/or diminishing of side effects. The method is especially suited to be used for the high throughput screening of numerous potential target compounds.

Compounds which modulate the peptidylarginine deiminase 6 function may be employed in therapeutic treatments by modulating the PAD of the present invention.

The invention also provides for a method for the formulation of a pharmaceutical composition comprising mixing the modulator compounds identified with a pharmaceutically acceptable carrier.

Pharmaceutical acceptable carriers are well known to those skilled in the art and include, for example, sterile saline, lactose, sucrose, calcium phosphate, gelatin, dextrin, agar, pectin, peanut oil, olive oil, sesame oil and water.

Furthermore the pharmaceutical composition may comprise one or more stabilizers such as, for example, carbohydrates including sorbitol, mannitol, starch, sucrosedextrin and glucose, proteins such as albumin or casein, and buffers like alkaline phosphates. Methods for making preparations and intravenous admixtures are disclosed in Remingtons's Pharmaceutical Sciences, pp. 1463–1497 (16th ed. 1980, Mack Publ. Co of Easton, Pa., USA).

Thus, the modulator compounds identified by using the peptidylarginine deiminase according to the invention are useful in the preparation of a pharmaceutical. The pharmaceutical is to be used for control of fertility disorders.

The following examples are illustrative for the invention and should in no way be interpreted as limiting the scope of the invention.

S=secondary follicle A=antral follicle

Figure 3:
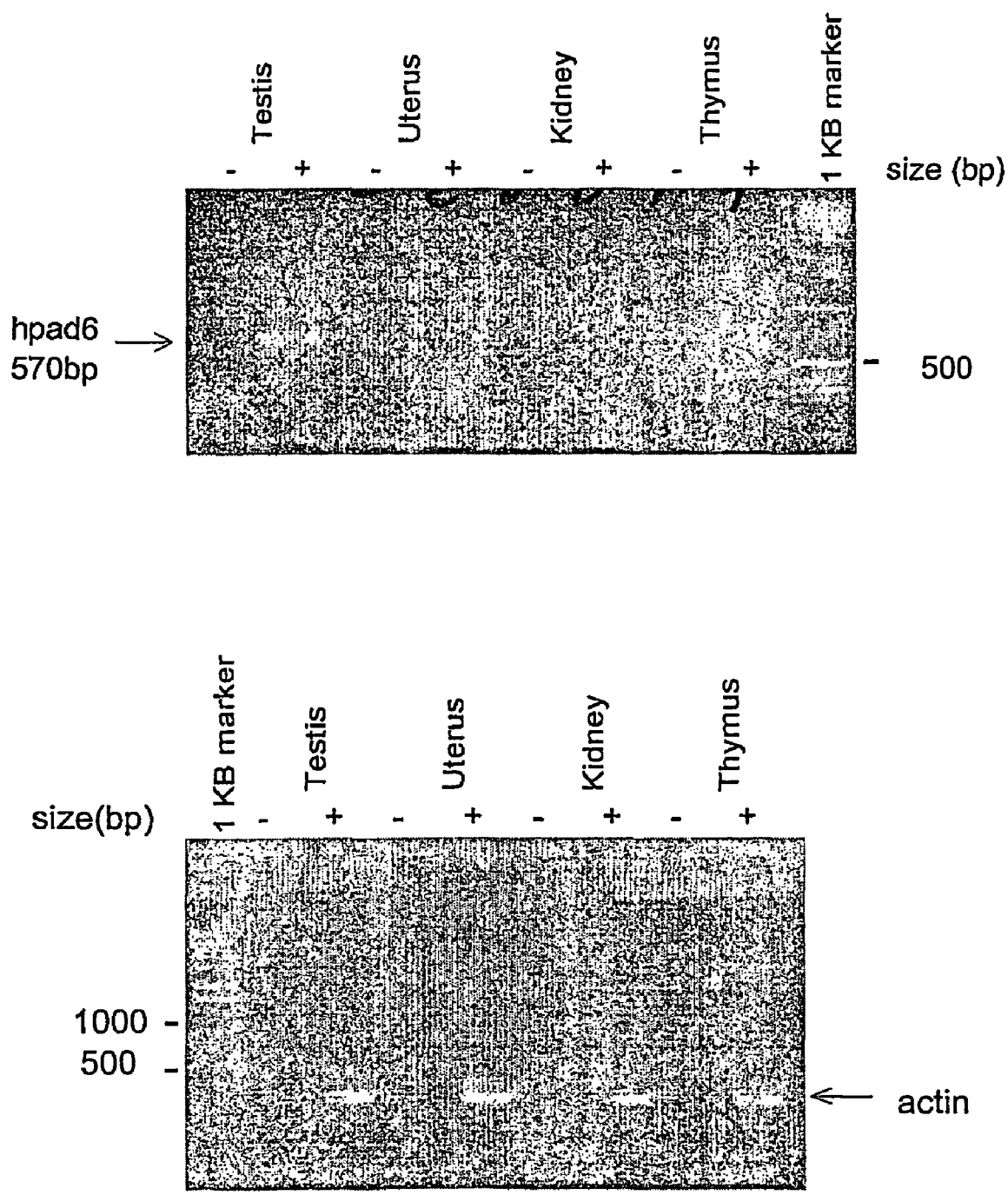

FIG. 3 RT-PCR analysis (30 cycles) of human PAD6 expression in various human tissues (upper panel). In the lower panel GAPDH controls in the absence and presence of RT are shown.

Figure 4:
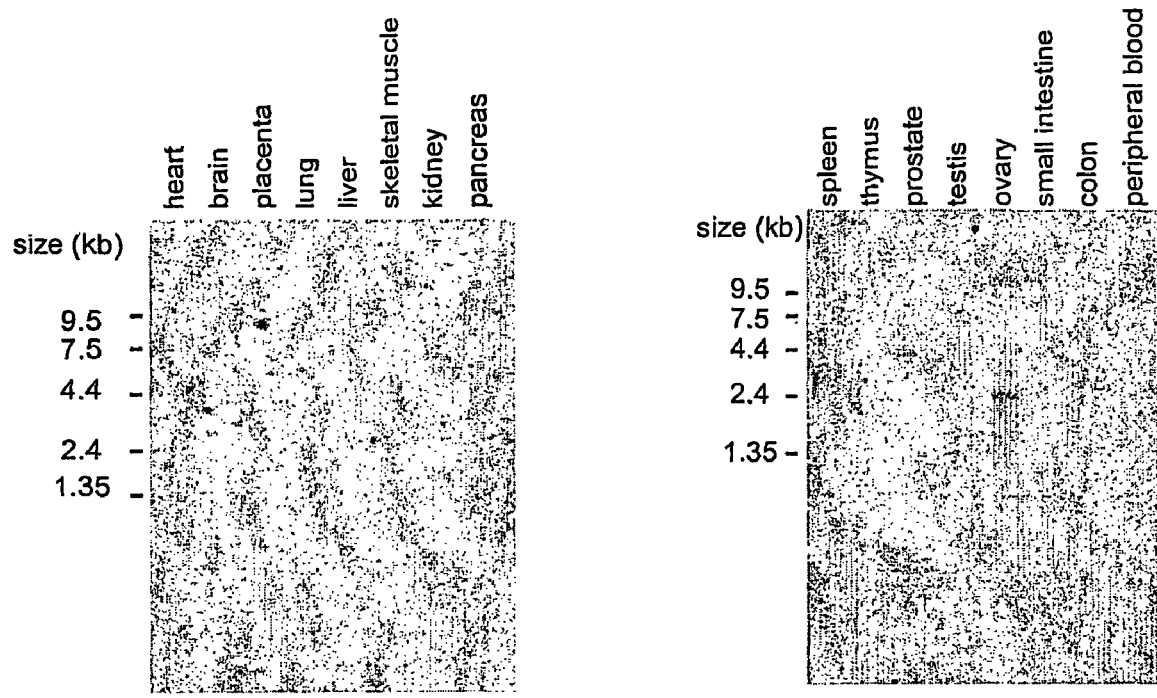

FIG. 4 Human multiple tissue northern blots (Clontech) hybridised with hPAD6 probe.

Figure 5:
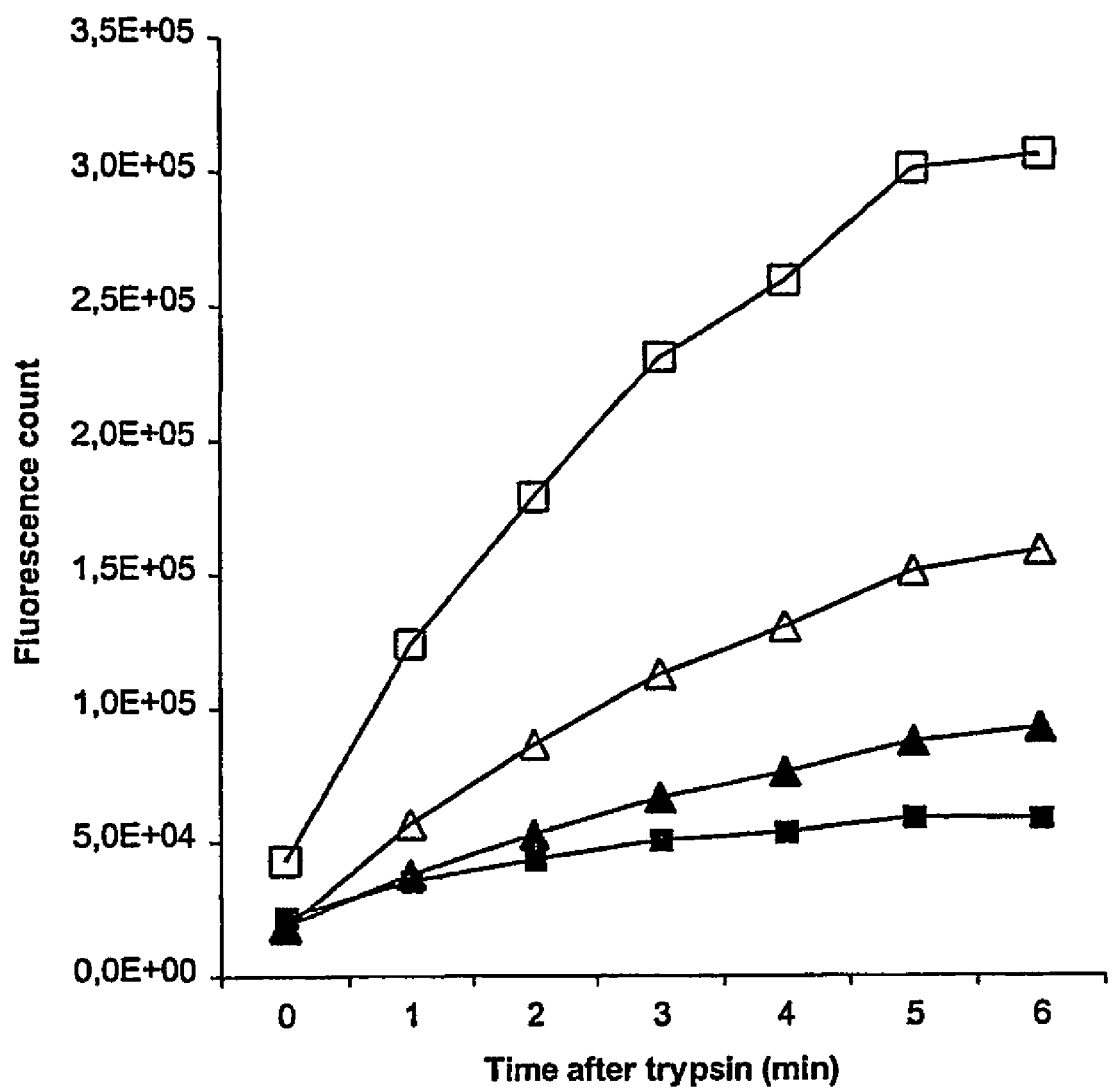

FIG. 5 Fluorescence measurement to determine PAD activity. STI (0.17 µg) was pre-incubated in the absence (filled square) or presence of 0.5 µg GST-PAD6 (filled triangle), 1.0 µg GST-PAD6 (open triangle), or 0.1 µg rabbit muscle PAD (open square; Sigma cat. No P1584) respectively. Subsequently, Nα-benzoyl-L-Arginine-7-amido-4-methylcoumarin (100 µM; Sigma cat. No. B7260) and trypsin (0.25 µg) were added, and fluorescence determined.

EXAMPLES

Example 1

Preparation of Mouse cDNA Clones

Generation of Oocyte cDNA Library.

Total RNA was isolated from 2172 denuded mouse oocytes, treated in vitro for 15 h with 50 µM FF-MAS, according to the RNAzol B™ RNA isolation protocol (Campro scientific). RNAzol B Was added directly to the frozen cell pellets containing approximately 100 oocytes each. Homogenates were pooled and extracted with 0.1 volume of chloroform, shaken for 15 seconds and incubated on ice for 10 minutes.

After centrifugation for 15 minutes at 14000 rpm at 4° C. the aqueous phase was collected. Total RNA was precipitated by adding an equal volume of isopropanol followed by o/n incubation at 4° C. RNA was centrifuged for 45 minutes at 14000 rpm at 4° C., the pellet was washed once with 700 µl of 70% ethanol followed by centrifugation at 14000 rpm at 4° C. for 30 minutes. The air-dried pellet was finally resuspended in 7.5 µl Rnase free water (Ambion). The total amount of RNA isolated using this procedure was determined using the Ribogreen™ RNA quantitation kit (Molecular Probes).

For cDNA synthesis, the SMART™ PCR library construction kit (Clontech) was used. The following modifications were introduced. An oligodT(18) primer with EcoRI restriction site (Pharmacia) was annealed to the 3' end of the mRNA and the SMART™ oligo extended with an EcoRI restriction site was annealed to the 5' end of the mRNA. The first strand cDNA synthesis reaction was in a reaction buffer containing 50 mM Tris (pH 8.3), 75 mM KCl, 6 mM MgCl$_2$, 2 mM DTT, 1 mM DNTP mix and 200 units Superscript ll RNase H Reverse transcriptase (Gibco BRL) for 1 hour at 42° C. Subsequently first strand cDNA was amplified by PCR using a Perkin Ehner thermocycler (9600). The PCR was performed in a total volume of 100 µl reaction buffer containing 1×Klen Taq PCR buffer (Clontech), 0.2 mM DNTP mix (Clontech), 0.2 mM 5' EcoRI-SMART primer, 0.2 mM NotI-EcoRI-dT (18) primer (Pharmacia) and 1×Advantage Kien Taq Polymerase Mix (Clontech) starting with 1 minute denaturation at 95° C. followed by 28 cycles of 15 seconds at 95° C. and 5 minutes at 68° C.

After purification on a Qiaquick spin column (QIAGEN) the cDNA was digested with EcoRI (Pharmacia) at 37° C. followed by heat inactivation at 70° C. for 10 minutes. cDNA was purified twice using two subsequent Qiaquick spin columns and finally resuspended in 50 µl 10 mM Tris-CL (pH 8.5). DNA concentration was determined by measuring adsorbance at 260 nm using a Genequant spectrophotometer.

Size fractionation of cDNA cDNA was size fractionated using agarose gel electrophoresis and extracted from the gel matrix using the Qiaexll Agarose Gel Extraction Kit (Qiagen). DNA was eluted in 20 µl H$_2$O, purified on a Qiaquick spin column (Qiagen) and eluted in 50 µl H$_2$O. The samples were precipitated by adding 0.1 volume of 3M Sodium Acetate, 10 µg of glycogen and 2.5 volumes of ethanol (96% v/v) followed by 1 h incubation at −20° C. The size fractionated cDNA was collected by centrifuigation at 14.000 rpm for 20 minutes at 4° C. The DNA pellet was washed with 70% ethanol and air dried before it was dissolved in MQ. DNA concentration was determined using the PicoGreen™ dsDNA Quantitation Kit (Molecular Probes).

After EcoRI digestion, 200 ng oocyte cDNA was ligated into 500 ng of predigested and dephosphorylated λXGT11 phage arms in a buffer containing 50 mM Tris-Cl pH 7.8, 10 mM MgCl$_2$, 10 mM dithiotreitol, 1 mM ATP, and 750 units/ml T4 ligase (Pharmacia). The reactions were incubated o/n at 16° C. The complete ligation reaction was finally packaged into a Max Plaxr™ packaging extract (Epicentre) as described in the product information sheet.

Example 2

Isolation and Characterization of Mouse PAD6

PCR Amplification of Phage Clones

Single plaques were incubated for at least one hour in 100 µl λ phage buffer (10 mM Tris-HCL pH 8.3, 100 mM NaCl$_2$ and 10 mM MgCl$_2$). From each eluted plaque 2.5 µl was PCR-amplified using λGT11 primers (SEQ ID NO:5 and SEQ ID NO:6). PCR reactions were performed on the PE9700 (9600 mode, Perkin Elmer), one cycle of 5 min at 94° C., 30 cycles of 30 sec at 94° C., 30 sec at 55° C. and 3 min at 72° C., followed by one cycle of 5 min at 72° C. PCR products were analyzed by agargse gel electrophoresis and selected on size, purity and concentration. Only single bands of 500 bp or more were selected for sequencing.

DNA Sequence Analysis 750 clones from the mouse oocyte cDNA library were analyzed by DNA sequencing after insert amplification by PCR. Sequence analysis was performed using the Big Dye DNA sequencing ready reaction protocol (Perkin Elmer) and samples were analyzed on the ABI377 automatic DNA sequencer (Perkin Elmer). Sequences were blasted against several databases a.o.: gblllrod, genpept, EMrodESTs59 and EMhumanESTs59 databases using BLASTN or TBLASTN in an automated procedure and annotated on basis of homology to gene(s) with known functions.

Identification and Characterization of PAD6.

One of the sequences obtained shows strong homology with peptidyl arginine deiminase III. Based on homology searches it has been established that this clone, 1B11, encodes a novel peptidyl argine deiminase that has been termed PAD6.

The 5'-end of mouse PAD6 cDNA could be amplified from a mouse ovary cDNA library. The cDNA of this library had been cloned directionally into NotI-SalI sites (5'–3') of the pSPORT vector (Life Technologies). This vector contains the M13 forward and SP6 promotor sequences 5' from the NotI site which have been used in the 5' RACE PCR in combination with two PAD6 specific reverse primers. The first PCR was performed with the M13F primer (SEQ ID NO:7) and the gene specific reverse primer (SEQ ID NO:8). This PCR product was diluted fifty times and one microliter of this dilution was used as template in the nested PCR with the SP6 primer (SEQ ID NO:9) and the nested gene specific reverse primer (SEQ ID NO:10). Both PCR reactions were performed in a total volume of 50 µl reaction buffer containing 1× Klen Taq PCR buffer (Clontech), 0.2 mM DNTP mix (Clontech) and 1× Advantage Klen Taq Polymerase Mix (Clontech) starting with 5 minutes of denaturation at 94° C. followed by 30 cycles of 30 seconds at 94° C., 30 seconds at 56° C., 3 minutes at 72° C. with an final extension of 5 minutes at 72° C.

Bands in the nested PCR products were cloned in the TA Topo PCR2.1 vector (Invitrogen) following the product information sheet and sequenced. It was found that a 1800 bp 5' RACE fragment completed the mouse PAD6 clone. The sequence of the full-length mouse cDNA is given in SEQ ID NO:2.

Figure 1:
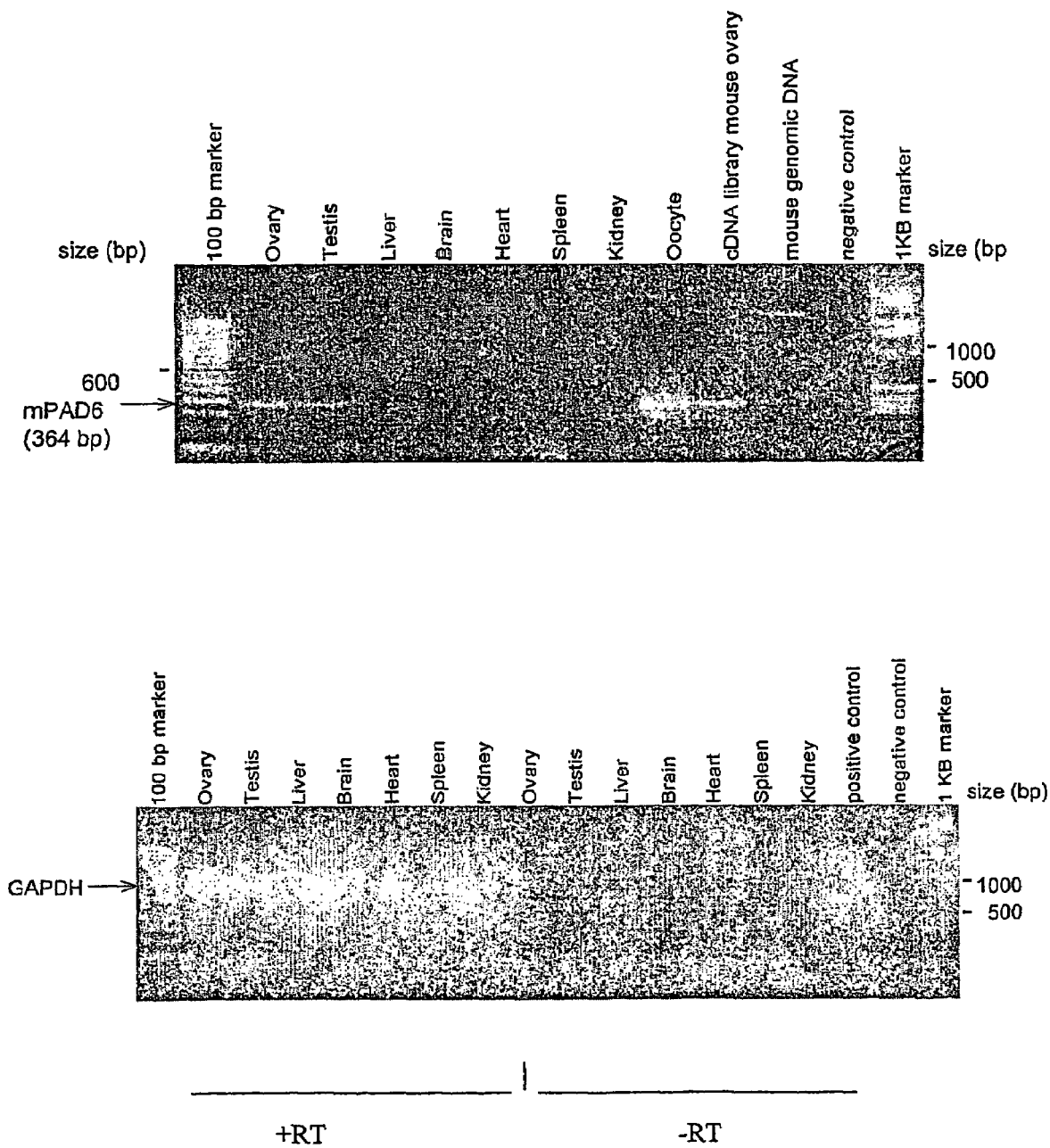
FIG. 1 RT-PCR analysis (30 cycles) of mouse PAD6 expression in various mouse tissues (upper panel). In the lower panel GAPDH controls in the absence and presence of RT are shown.

Based on DNA sequence information obtained, gene specific PCR primer sets were designed and used in RT-PCR experiments to confirm the tissue-specific expression profile. The data obtained (FIG. 1) confirm the oocyte/ovary- (and testis-)specific expression for mouse PAD6. (SEQ ID NO:8 and SEQ ID NO:13 were used as primers).

In Situ Hybridization (ISH)

To further study the expression of PAD6 in the gonads, in situ hybridization (ISH) was performed on sections of mouse ovary and testis.

Ovaries of day 7 and adult mice were fixed in 4% buffered formalin for 24 hours at room temperature. The tissues were embedded in paraffin. Paraffin sections (5 µm) were cut, mounted on Superfrost plus microscope slides, and allowed to dry overnight at 37° C. The slides were baked at 60° C. for two hours.

Tissue sections were dewaxed in xylene en rehydrated in descending concentrations of ethanol. Slides were washed for 20 min shaking in 0.2M HCl, followed by two washes in DEPC (di-ethylpyrocarbonate) treated Milli Q. The sections were treated with proteinase K (1 µg/ml) in digest buffer (100 mM Tris, 50 mM EDTA pH 8) for 30 min at 37° C. Digestion was stopped in prechilled 0.2% glycine in PBS for 10 min shaking at room temperature (RT). The slides were acetylated for 5 min with 0.25% acetic anhydride in 0.1 M triethanolamine buffer, followed by two washes in DEPC treated Milli Q. Sections were prehybridised at hybridisation temperature in a humid chamber with prehybridisation mix, containing 52% formamide, 21 mM Tris, 1 mM EDTA, 0.33 M NaCl, 10% dextran sulphate, 1× Denhardt's solution, 100 µg/ml salmon sperm DNAI 100 µg/ml tNA and 250 µg/ml yeast total RNA. The slides were covered with a glass coverslip. After two hours coverslips were replaced by coverslips holding 100 µl probe hybridization mix, containing prehybridization mix with the following additions: 0.1 mM DTT, 0.1% sodium thiosulphate, 0.1% SDS and 200 ng/ml DIG-labeled probe.

DIG-labeled probes were generated by in vitro transcription from a linear DNA template, using DIG-dUTP and DNA-dependent RNA polymerases (SP6 and T7). The promoter site of each RNA polymerase was attached to gene specific sequences allowing the generation of a PCR fragment containing the SP6 promoter site at the 5' and the T7 promoter at the 3' site. In general, probes from about 250–500 nucleotides were made located at the 5' end of SEQ ID NO:2. After in vitro transcription a small amount of the probe was analyzed on a 1.5% agarose gel to confirm successful in vitro transcription. Probe concentrations were estimated by spotting serial dilutions (including control DIG-RNA (100 ng/µl)) on a Hybond N+ membrane followed by is anti-DIG alkaline phosphatase Fab' fragments (anti-DIG-AP) and NBT/BCIP colour substrate incubation.

The hybridization was carried out overnight (16 hours) in a humid chamber at 42° C. or 50° C. Slides were then washed in 2×SSC, shaking for 15 min, followed by washes in 2×SSC, 1×SSC and 0.1×SSC for 15 min shaking at hybridization temperature. Sections were digested by Ribonuclease A (20 µg/ml) in RNase buffer (0.6 M NaCl, 20 µM Tris, 10 mM EDTA) for 1 hour at 37° C. After two washes (5 min shaking RT) in prechilled PBS and one wash in buffer 1 (100 mM maleic acid, 150 mM NaCl), the sections were incubated for 30 min with blocking solution (1 g/ml blocking reagent in buffer 1). Then the sections were incubated with anti-DIG-AP, diluted 1:500 in blocking solution, for 1 hour at RT. After two washes in buffer 1 (15 min shaking RT), the slides were carefully wiped dry around the tissue and the sections were encircled with a DAKO-pen. The sections were covered with NBT/BCIP colour development reagent and incubated in a humid chamber at RT. After two hours the sections were examined under a microscope. If no or only weak staining was observed the incubation was continued overnight at 4° C. and the next day at RT. Finally, the slides were rinsed in water and optionally counterstained with Mayer's hematoxyline 1:5 for three seconds. Slides were mounted in Kaisers glycerol gelatin.

Figure 2:
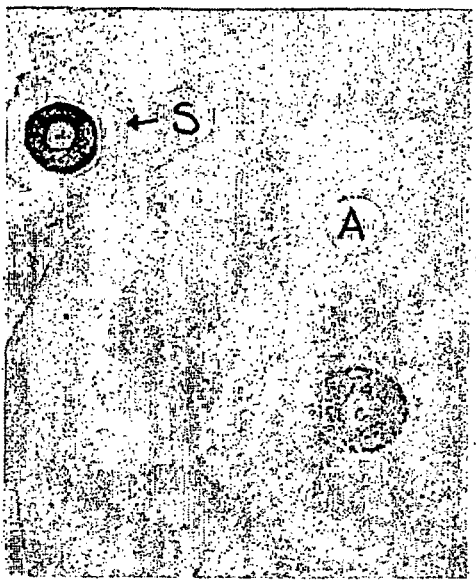
FIG. 2 ISH (In Situ Hybridization) analysis using clone 1B11 asa probe on ovaries from young (7 days) and adult mice.
Figure 2:
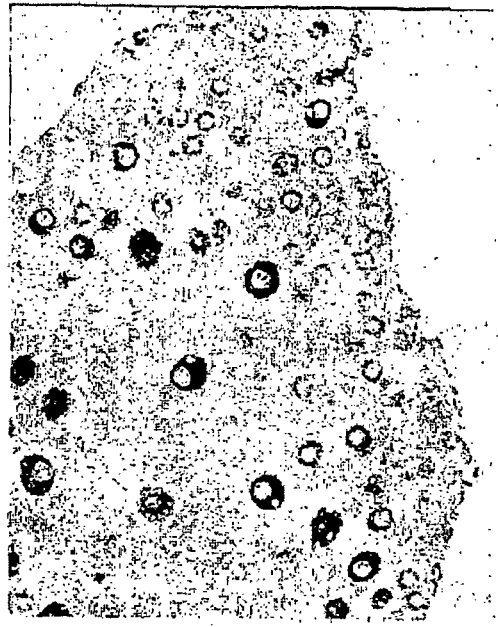
Figure 2:
Figure 2:

As shown in FIG. 2, PAD6 is expressed in the ovary exclusively in oocytes.

PAD6 mRNA has high expression levels in oocytes of primary, secondary and antral follicles, but is also expressed in oocytes from primordial follicles. Based on the data obtained so far the expression level of PAD6 mRNA decreases in oocytes of antral follicles suggesting that the function of PAD6 is most likely required during early stages of oogenesis. Although RT-PCR data revealed testis expression of PAD6, no expression above background level of PAD6 mRNA was detected using ISH analysis suggesting low levels of expression of PAD6 in the testis.

Example 3

Isolation and Characterization of Human PAD6

A BLAST search using the fall-length mouse PAD6 cDNA as a query against the EM63hsGeno(new) databases identified the human homologue of PAD6. This search only identified the C-terminal region of the coding sequence of human PAD6. To extend the sequence in the 5' direction primers were designed and a 5' RACE PCR was performed on human ovary Marathon Ready cDNA (Clontech) using the Marathon Ready™ cDNA user manual. The first PCR was performed under the following conditions: a denaturation of 30 seconds at 94° C., 5 cycles of 5 seconds at 94° C. and 3 minutes at 72° C., 5 cycles of 5 seconds at 94° C. and 3 minutes at 70° C. and 25 cycles of 5 seconds at 94° C. and 3 minutes at 68° C. A 50-fold dilution of this first PCR product served as template in the second, nested PCR reaction using the same PCR conditions. An expected band of ≈650 bp was cloned in the TA Topo PCR2.1 vector (Invitrogen) and sequenced. This clone contained (by homology) the first 5' 500 base pairs of the coding sequence of human PAD6, thus completing the coding sequence of human PAD6.

PCR primers were selected to amplify the full length human PAD6 cDNA human ovary RNA. For isolation of human PAD6 cDNA the primers SEQ ID NO: 11 and SEQ ID NO:12 were used on Marathon Ready ovary cDNA (Clontech). PCR conditions were: denaturation for 5 minutes at 94° C. followed by 5 cycles of 30 seconds at 94° C. and 3 minutes at 68° C., 28 cycles of 30 seconds at 94° C., 30 seconds at 62° C. and 3 minutes at 72° C. with a final extension of 7 minutes at 72° C.

The full length amplificates of three independent PCR reaction were cloned into the PCR2.1 Topo vector (Invitrogen) and sequenced to determine the consensus nucleotide sequences. Its sequence is shown in SEQ ID NO:4.

Gene specific PCR primer sets were designed (SEQ ID NO:14 and SEQ ID NO: 15) and used in RT-PCR experiments to determine the expression profile of human PAD6. RT-PCR on RNA from human testis, uterus, kidney, thymus, liver, brain, heart, lung and spleen, revealed PAD6 expression only in testis (FIG. 3).

Multiple Tissue Northern Blots (Clontech) of human tissues were hybridised with the PCR fragment of human PAD6 (approximately 590 bp; PCR product of primers SEQ ID No: 14 and SEQ ID NO:15 extending from nucleotides 464–1052 in SEQ ID NO:4). Probes were labelled with [$^{32}$P]dCTP and Ready to Go Labellings beads (AP Biotech) according to the manufacturer's instruction using an incubation time of 60 minutes at 37° C. The non-incorporated dNTP's were removed on a spin column of Sephadex G50 in a 1 ml syringe.

The blots were prehybridised in Express hybmix (Clontech) for at least one hour at 65° C. For hybridisation 4–8×10$^7$ cpm of the denaturated probes were added to the prehybridisation mixture. The blots were hybridised at 65° C. overnight and washed once with 2×SSC, 0.1% SDS at room temperature, twice with 1×SSC, 0.1% SDS at 65° C. and once with 0.1×SSC, 0.1% SDS at 65° C. The hybridised blots were analysed with the STORM 840 Phosphor imager (Molecular Dynamics), scanned on 200 micron and printed with a range of 0–50 after exposure of three days to Kodak storage phosphor screens GP (Molecular dynamics).

In FIG. 4 a single band in ovary with an estimated length of about 3 kB can be seen showing up only in ovary. No signal could be detected in testis, most likely because the level of PAD6 expression in testis is too low to be detected on Northern blots. In situ hybridisation analysis corroborates these results: PAD6 expression could be detected in all types of follicles of human and monkey ovaries and are in this respect similar to the in situ data in mouse. By in situ hybridisation no expression was detected in testis (data not shown).

Example 4

Expression of human PAD6 and determination of PAD6 activity

Cloning

Full-length human PAD6 was cloned into the bacterial expression vector pGEX4T1 (AP Biotech) using the Rapid DNA Ligation kit (Boehringer). The recombinant construct (pGEXhPAD6) was characterised by restriction enzyme digestion. *E. coli* BL-21 cells transformed with pGEXhPAD6 were grown in 2×YT medium at 25° C. to a cell density of 1.0 at 650 nm. After addition of 0.1 mM isopropyl-β-D-thiogalactopyranoside the culture was grown for an additional 5 hours at 25° C. The cells were centrifuged and resuspended in 0.1 vol of the original culture volume of 20 mM Tris-HCl, pH 7.6, 1 mM EDTA and lysed by sonication on ice. The sonicate was centrifuged at 15000×g for 30 minutes at 4° C. (Sorvall, SS34 rotor) and to the supernatant 1M NaCl, 0.1% of Triton X-100 and 50% glutathion-Sepharose 4B beads in PBS (Pharmacia Biotech, 1 ml to an equivalent of 250 ml initial culture) was added, followed by incubation at 4° C. for 60 minutes with gentle agitation. The beads were then washed three times with 10 bed volumes of a buffer containing 20 mM Tris-HCl pH 7.6, 1 mM EDTA, 0.1% Triton X-100 and 0.1 M NaCl at RT for 5 minutes with gentle agitation. The recombinant hPAD6-gst fusion protein was eluted from the beads in several steps with 10 to 100 mM reduced glutathione in 50 mM Tris-Cl pH 8.0, 0.1 M NaCl and 0.1% Triton X-100 at 4° C. for 30 minutes with gentle agitation. The eluates were stored with 10% glycerol at −20° C. for determination of enzymatic activity. The purity of the protein was estimated to be 90% based on SDS PAGE analysis.

Determination of PAD6 Enzyme Activity.

The activity of the PAD was determined by the formation of citrulline in Soybean Trypsin Inhibitor (STI) as a substrate. In contrast to the original STI, citrullinated STI is unable to inhibit trypsin activity. Therefore, an increased activity of trypsin, as detected with a fluorescent trypsin substrate, indicates PAD activity.

For PAD activity, the reaction mixture consisted of 100 mM HEPES (H 7.5), 5 mM CaCl2, 2 mM DTT, 0.17 μg STI and an aliquot of the purified enzyme solution [either GST-PAD6 or the commercial available PAD (Sigma), derived form rabbit muscle] in a final volume of 20 μl. After incubation of the assay mixture for 30 minutes at 37° C., 10 μl of the fluorescent substrate Na-benzoyl-L-Arginine-7-amido-4-methylcoumarin [400 μM in 100 mM HEPES (pH 7.5), 50 μM EDTA] and 10 μl of trypsin solution [0.25 μg in 100 mM HEPES (pH 7.5)] were added subsequently. Fluorescence measurements (excitation 360 um, emission 460 nm) were started directly in a Victor V at room temperature, and were continued for one hour.

PAD6 activity could be detected as can be seen in FIG. 5.

We claim:

1. An isolated polynucleotide encoding the polypeptide of SEQ ID NO:3.

2. A polynucleotide according to claim 1, wherein said polynucleotide comprises the nucleotides 20–2077 of SEQ ID NO:4.

3. A recombinant expression vector comprising the polynucleotide according to claim 1.

4. The recombinant expression vector of claim 3, wherein the polynucleotide comprises the nucleotides 20–2077 of SEQ ID NO:4.

5. An isolated cell transfected with a polynucleotide according to claim 1.

6. The isolated cell of claim 5, wherein the polynucleotide comprises the nucleotides 20–2077 of SEQ ID NO:4.

7. An isolated cell transfected with a recombinant expression vector according to claim 3.

8. The isolated cell of claim 5, wherein the transfected cell expresses the polypeptide of SEQ ID NO:3.

9. The isolated cell of claim 7, wherein the transfected cell expresses the polypeptide of SEQ ID NO:3.

10. A method to produce the polypeptide of SEQ ID NO:3, comprising culturing the isolated cell of claim 8 under conditions wherein said polypeptide is produced and recovering said polypeptide from the culture.

11. A method to produce the polypeptide of SEQ ID NO:3, comprising culturing the isolated cell of claim 9 under conditions wherein said polypeptide is produced and recovering said polypeptide from the culture.

12. An isolated nucleic acid encoding a polypeptide having at least 95% sequence identity with SEQ ID NO: 3, wherein said polypeptide has peptidylarginine deiminase activity.

13. The isolated nucleic acid of claim 12, wherein the isolated nucleic acid is of human origin.

* * * * *